United States Patent [19]
Jacobson et al.

[11] Patent Number: 6,147,062
[45] Date of Patent: Nov. 14, 2000

[54] PHOSPHORYL HYDRAZINE INSECTICIDES

[75] Inventors: Richard Martin Jacobson, Chalfont; Luong Tu Nguyen, Lansdale, both of Pa.

[73] Assignee: Rohm and Haas Company, Philadelphia, Pa.

[21] Appl. No.: 09/440,563

[22] Filed: Nov. 15, 1999

Related U.S. Application Data

[60] Provisional application No. 60/109,647, Nov. 24, 1998.
[51] Int. Cl.[7] .......................... A61P 33/10; A61K 31/664; A01N 57/28; C07F 9/24
[52] U.S. Cl. ........................... 514/118; 558/88; 558/144; 558/154
[58] Field of Search ............................. 558/88, 144, 154; 514/118

[56] References Cited

U.S. PATENT DOCUMENTS

| | | |
|---|---|---|
| 2,965,668 | 12/1960 | Tolkmith . |
| 4,203,932 | 5/1980 | Brown ..................................... 558/154 |
| 4,203,979 | 5/1980 | Brown . |
| 5,367,093 | 11/1994 | Dekeyser et al. . |

*Primary Examiner*—Michael G. Ambrose
*Attorney, Agent, or Firm*—Thomas D. Rogerson

[57] ABSTRACT

This invention relates to a new class of phosphoryl hydrazine compounds which are useful as insecticides, acaricides, anthelmintics, and nematocides, compositions containing the compounds, and methods for their use. This invention also relates to methods to produce such compounds.

10 Claims, No Drawings

PHOSPHORYL HYDRAZINE INSECTICIDES

This application claims the benefit of U.S. Provisional Application No. 60/109,647, which was filed on Nov. 24, 1998.

This invention relates to phosphoryl hydrazine compounds which are useful as insecticides, acaricides, nematocides, and anthelmintics, compositions containing the compounds, and methods for their use. This invention also relates to the preparation of such compounds.

The search for compounds which have a combination of excellent insecticidal activity and low undesirable toxicity is a continuing one because of factors such as the desire for compounds exhibiting greater activity, better selectivity, lower undesirable environmental impact, lower production and market cost and higher effectiveness against insects which are or become resistant to many known insecticides. In particular, there exists a need for effective agents to control soil dwelling insects and nematodes. Commercial insecticides, for example, chlorpyriphos and diazinon, have serious deficiencies such as requiring high application rates or possessing undesirable toxicity to non-target organisms including mammals, birds, and fish. Commercial nematocides are often highly toxic and/or environmentally unfriendly materials, for example, methyl bromide.

We have found a group of compounds which are effective for controlling insects under a variety of conditions. These compounds are particularly effective in controlling soil dwelling insects. In addition, these compounds have an added benefit in that they are also effective against acarids and nematodes. The compounds of the present invention have the further benefit of having anthelminthic activity.

The present invention provides a new class of insecticides of the general formula (I).

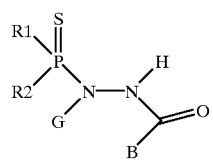

(I)

wherein:
R1 is unsubstituted or substituted ($C_1$–$C_6$) alkoxy wherein the substituents are independently one or more ($C_1$–$C_6$) alkoxy, keto, carbo($C_1$–$C_6$)alkoxy, or ($C_1$–$C_6$)acyl groups;

R2 is ($C_1$–$C_6$) alkoxy, ($C_1$–$C_6$) alkyl, or phenyl, each of which is unsubstituted or substituted with one or more ($C_1$–$C_6$) alkoxy, keto, carbo($C_1$–$C_6$)alkoxy, or ($C_1$–$C_6$) acyl groups;

G is ($C_3$–$C_6$) secondary alkyl or ($C_4$–$C_6$) tertiary alkyl, each of which is unsubstituted or substituted with one or more cyano, ($C_1$–$C_6$) alkoxy, carbo($C_1$–$C_6$)alkoxy, or ($C_1$–$C_6$)acyl groups;

B is ($C_1$–$C_6$) haloalkyl;

its enantiomers and stereoisomers;
and agronomically acceptable salts thereof.

The compounds of the present invention are particularly notable in that in addition to controlling insects they have also shown activity against acarids, nematodes, and helminths. The terms "control" or "controlling" mean adversely affecting the existence or growth of the pest at any stage in its life cycle. This includes complete killing, eradication, arresting or inhibiting growth or reproduction, reducing in number, or any combination thereof.

The term "halo" by itself or as a part of another substituent means chloro, fluoro, bromo and iodo.

The term "alkyl" by itself or as a part of another substituent, unless otherwise stated, means straight and branched chain groups such as methyl, ethyl, propyl, isopropyl, butyl, iso-butyl, sec-butyl, tert-butyl, pentyl, neopentyl, and hexyl.

The term "haloalkyl" by itself or as a part of another substituent is an alkyl group of the stated number of carbon atoms having one or more halo atoms bonded thereto such as chloromethyl, dichloromethyl, trichloromethyl, bromoethyl, trifluoromethyl, and bromodifluoromethyl.

Also provided are compositions comprising an agronomically or pharmaceutically acceptable carrier and a pesticidally or anthelmintically effective amount of one or more compounds of formula I; methods of using the compounds and compositions, and methods to prepare the compounds. For purpose of this invention, the term "pest" means insects, acarids, nematodes, and helminths. The term "effective amount" means an amount of compound which, when applied to a pest or to an area to be treated or dosed to a non-pest organism provides an acceptable level of control of a pest or pests.

The term "helminth" or "helminths" includes members of the phyla Nemathelminthes (for example; intestinal roundworms, hookworms, pinworms, and heartworms) and Platyhelminthes (for example; trematodes and cestodes). The term "anthelmintic" means adversely affecting the existence or growth of a any stage in its life cycle.

The compounds and compositions of the present invention are pesticidally active against a variety of insects, acarids, and nematodes, particularly soil insects such as corn rootworms and soil nematodes. Therefore, this invention also provides a method of controlling such pests which comprises applying to the pest or to the soil or to the foliage of plants to be freed from infestation by the pest, or pesticidally effective amount of one or more compounds of formula I or a composition comprising one or more compounds of formula I.

Examples of compounds of formula I include those listed in Table 1.

TABLE 1

| # | R1 | R2 | G | B |
|---|---|---|---|---|
| 1 | $OCH_2CH_3$ | $OCH_2CH_3$ | $C(CH_3)_3$ | $CCl_3$ |
| 2 | $OCH_2CH_2CH_3$ | $OCH_2CH_2CH_3$ | $C(CH_3)_3$ | $CCl_3$ |
| 3 | $OCH_2CH_3$ | $OCH_2CH_2CH_3$ | $C(CH_3)_3$ | $CCl_3$ |
| 4 | $OCH_2CH_3$ | $OCH_2C(CH_3)_3$ | $C(CH_3)_3$ | $CCl_3$ |
| 5 | $OCH_2CH_3$ | $OCH(CH_3)CH_2CH_3$ | $C(CH_3)_3$ | $CCl_3$ |
| 6 | $OCH_2CH_3$ | $OCH(CH_3)_2$ | $C(CH_3)_3$ | $CCl_3$ |
| 7 | $OCH_2CH_3$ | $OCH_2CH_3$ | $C(CH_3)_3$ | $CCl_2F$ |
| 8 | $OCH_2CH_3$ | $OCH_2CH_3$ | $C(CH_3)_3$ | $CBr_3$ |
| 9 | $OCH_3$ | $OCH_3$ | $C(CH_3)_3$ | $CCl_3$ |
| 10 | $OCH_2CH_3$ | $OCH_2CH_3$ | $C(CH_3)_3$ | $CHCl_2$ |
| 11 | $OCH_2CH_3$ | $OCH_2CH_3$ | $C(CH_3)_3$ | $CH_2Cl$ |
| 12 | $OCH_2CH_3$ | $OCH_2CH_3$ | $C(CH_3)_3$ | $CF_3$ |
| 13 | $OCH_3$ | $OCH_3$ | $C(CH_3)_3$ | $CHCl_2$ |
| 14 | $OCH_3$ | $OCH_3$ | $C(CH_3)_3$ | $CH_2Cl$ |
| 15 | $OCH_2CH_3$ | $OCH_2CH_3$ | $C(CH_3)_3$ | $CClF_2$ |
| 16 | $OCH_2CH_2OCH_3$ | $OCH_2CH_2OCH_3$ | $C(CH_3)_3$ | $CCl_3$ |
| 17 | $OCH_2CH_2OCH_3$ | $OCH_2CH_2OCH_3$ | $C(CH_3)_3$ | $CHCl_2$ |
| 18 | $OCH_2CH_3$ | $OCH_2CH_2OCH_3$ | $C(CH_3)_3$ | $CCl_3$ |
| 19 | $OCH_2CH_3$ | $OCH_2CH_2OCH_3$ | $C(CH_3)_3$ | $CHCl_2$ |
| 20 | $OCH_2CH_3$ | $CH_3$ | $C(CH_3)_3$ | $CCl_3$ |
| 21 | $OCH_2CH_3$ | $CH_2CH_3$ | $C(CH_3)_3$ | $CCl_3$ |
| 22 | $OCH_2CH_3$ | PHENYL | $C(CH_3)_3$ | $CCl_3$ |
| 23 | $OCH_2CH_3$ | $CH_2CH_3$ | $C(CH_3)_3$ | $CHCl_2$ |

# = Compound Number

Preferred compounds of formula I are those wherein R1 and R2 are independently selected from ($C_1$–$C_2$)alkoxy; G is ($C_4$–$C_6$)tertiary alkyl, and B is halo($C_1$)alkyl. Most preferred are compounds wherein R1 and R2 are identical and selected from methoxy and ethoxy, G is tertiary butyl, and B is dichlormethyl or trichloromethyl.

The compositions and compounds of this invention can be applied directly to the locus to be protected, for example, the area around or upon plants infected with insects or nematodes or to plants on which infestation is to be prevented. The compounds and compositions may be used either as contact or systemic pesticides.

To control pests, the active compound may be applied to soil or to plant foliage. When applied to foliage, it may be absorbed by the plant, translocated to other parts and ultimately ingested by the pest by means of ingestion of the plant part(s). This means of application is referred to as "systemic" application. Alternatively, the compound may be foliarly applied to the plants to be freed from insects and other pests which feed on the foliage. In another alternative, the active compound may be applied to the soil and contacted therein with the pest to be controlled. This means of application is referred to as "soil" application.

The compounds of this invention are especially effective against soil pests when applied on or incorporated into the soil in order to effect direct contact with the pests.

The compositions of the present invention can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, the pesticide application rate, and the pests to be controlled. It may be desirable to include one or more additional adjuvants in the spray tank. Such adjuvants include, for example, surfactants, dispersants, spreaders, stickers, antifoam agents, emulsifiers, and other similar materials such as described in *McCutcheon's Emulsifiers and Detergents, McCutcheon's Emulsifiers and Detergents/Functional Materials,* and *McCutcheon's Functional Materials,* all published annually by McCutcheon Division of MC Publishing Company (New Jersey).

The compounds and compositions of the present invention can also be mixed with fertilizers or fertilizing materials before their application. In one type of solid fertilizing composition, particles of a fertilizer or fertilizing ingredients, such as ammonium sulfate, ammonium nitrate, or ammonium phosphate, can be coated with one or more of the compounds or compositions. The compounds or compositions and solid fertilizing material can also be admixed in mixing or blending equipment, or they can be incorporated with fertilizers in granular formulations. Any relative proportion of fertilizer can be used which is suitable for the crops to be treated. The compounds or compositions of this invention will commonly comprise from 5% to 50% of the fertilizing composition. Such pesticide/fertilizer compositions provide fertilizing materials which promote the rapid growth of desired plants, and at the same time control pests. Unless otherwise specified, all percentages are percentages by weight.

By "agronomically acceptable carrier" is meant any substance or mixture of substances which can be utilized to dissolve, disperse or diffuse the compound incorporated therein without impairing the effectiveness of the compound and which does not create permanent damage to soil, equipment, and agronomic crops when utilized according to recommendations.

The compounds of this invention can be taken up on or mixed with a finely divided solid carrier, as for example, clays, inorganic silicates, carbonates, and silicas. Organic carriers can also be employed.

Dust concentrates are commonly made wherein pesticidal compounds are present in the range of about 20% to 80%. For ultimate applications, these concentrates are normally extended with additional solid to give a pesticide active ingredient content of from 0.1 to about 20%. Granular formulations are made using a granular or pelletized form of carrier, such as granular clays, vermiculite, charcoal or corn cobs, and may contain the active ingredient from about 1 to about 25% by weight.

Wettable powder formulations are commonly made by incorporating one or more pesticidal compounds in an inert, finely divided solid carrier along with a surfactant which can be one or more emulsifying, wetting, dispersing, or spreading agents or a blend of these. The compounds are usually present in the range of about 10 to about 80% by weight and surfactants in the range of from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such material as glycerol mannitan laureate and a condensate of polygylcerol and oleic acid modified with phthalic anhydride. Dispersing agents include such materials as the sodium salt of the copolymer of maleic anhydride and an olefin such as diisobutylene, sodium lignin sulfonate and sodium formaldehyde naphthalene sulfonates.

Water dispersible granular products may be prepared by granulating or agglomerating a suitable wettable powder formulation which is compatible with the active ingredients. Agglomeration is typically carried out in a conventional manner such as by a pan agglomerator. Dispersible granular products are described in U.S. Pat. No. 3,954,439 and British Pat. No. 1,433,882.

One convenient method for preparing a solid formulation, e.g. dust, wettable powder, or granular, is to impregnate one or more compounds of this invention onto a solid carrier by means of a volatile solvent, such as acetone. In this manner, adjuvants, such as activators, adhesives, plant nutrients, synergists and various surfactants can also be incorporated.

Emulsifiable concentrate formulations are prepared by dissolving one or more pesticidal compounds in an agronomically acceptable organic solvent and adding a solvent-soluble emulsifying agent. Suitable solvents are usually water-immiscible and can be found in the hydrocarbon, chlorinated hydrocarbon, ketone, ester, alcohol and amide classes of organic solvents. Mixtures of solvents are commonly employed. The surfactants useful as emulsifying agents may constitute from 0.5 to 10% by weight of emulsifiable concentrates and may be anionic, cationic or nonionic in character. The concentration of the compounds may vary from 10 to 80%, preferably in the range of from 25 to 50%.

For use as pesticidal agents, the compounds of this invention should be applied in an effective amount sufficient to exert the desired pesticidal activity by techniques well known in the art. In certain situations, however, it may be desirable and advantageous to apply the compounds directly onto the loci to be protected or freed of pests without the benefit of any substantial amount of carrier. This is a particularly effective method when the physical nature of the particular compound or compounds is such as to permit what is known as "low-volume" application, that is, when the compounds are in liquid form or substantially soluble in higher boiling solvents.

The application rate will vary depending upon the purpose of such application, the compound being utilized, the frequency of dissemination, and the like. For use as insecticides or acaricides, dilute sprays can be applied at concentrations of from 0.01 to 50 kg of the compound per 400 liters of spray. They are usually applied at from 0.1 to 20 kg per 100 liters. In more concentrated sprays, the active ingredient is increased by a factor of 2 to 40. With dilute sprays, applications are usually made to the plants until run-off is achieved, whereas with more concentrated or low-volume sprays, the materials are more commonly applied as mists.

For use as a soil insecticide, the compounds can be applied as dilute liquid preparations or as solid formulations, preferably granular formulations, by broadcasting, side-dressing, introduction into the seed furrow, soil incorporation, or seed treatment. The application rate can be from 0.05 to 10 kg per hectare of the compound and for economic reasons, preferably from 0.1 to 2 kg per hectare.

The compounds of this invention can be utilized as the sole pesticidal agents or they can be employed in conjunction with other pesticidal agents such as, for example, microbiocides, fungicides, herbicides, insecticides, acaricides, and the like.

Examples of pesticides which can be combined in the compositions of the present invention include: (1) fungicides such as, for example, (a) dithiocarbamates and derivatives; (b) nitrophenol derivatives; (c) heterocyclic structures; (d) miscellaneous halogenated fungicides; (e) fungicidal antibiotics; (f) copper-based fungicides; and (g) methoxyacrylates; (2) herbicides, such as, (a) carboxylic acid derivatives; (b) carbamic acid derivatives; (c) substituted ureas, (d) substituted triazines, (e) diphenyl ethers; (f) anilides; (g) oxyphenoxy herbicides; (h) uracils; (i) nitriles; and (j) other organic herbicides; and (3) insecticides, such as, (a) organochlorines, (b) organophosphates, (c) carbamates, (d) botanicals, (e) synthetic pyrethroids, (f) formamidines, (g) dinitrophenols (h) organotins, (i) acylureas, (j) acylhydrazines, (k) juvenile hormone mimics, (l) viruses, (m) antibiotics, (n) neonicotinoids, (o) funigants, (p) insect repellents, (q) inorganics, and (r) insecticidal soaps.

For anthelmintic use, the compounds described herein may be taken up in pharmaceutically acceptable carriers, such as, for example, solutions, suspensions, tablets, capsules, ointments, elixirs and injectable compositions. Pharmaceutical preparations may contain from 0.1% to 99% of the active ingredient. Preparations which are in single dose form, "unit dosage form", preferably contain from 20% to 90% active ingredient, and preparations which are not in single dose form preferably contain from 5% to 20% active ingredient. As used herein, the term "active ingredient" refers to compounds described herein, salts thereof, and mixtures of compounds described herein with other pharmaceutically active compounds. Dosage unit forms such as, for example, tablets or capsules, typically contain from about 0.05 to about 1.0 g of active ingredient.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

The compounds described herein may be administered alone or in conjunction with other pharmaceutically active compounds. It will be understood by those skilled in the art that pharmaceutically active compounds to be used in combination with the compounds described herein will be selected in order to avoid adverse effects on the recipient or undesirable interactions between the compounds.

While the compounds described herein may be administered alone for anthelmintic use, it is preferable to administer them as pharmaceutical formulations. Useful formulations comprise one or more active ingredients and one or more pharmaceutically acceptable carriers. The term "pharmaceutically acceptable" means compatible with the other ingredients of the formulation and not toxic to the recipient. The formulations may conveniently be prepared in unit dosage form and may be prepared by any method known in the art of pharmacy. Such methods include the step of bringing the active ingredient into association with the carrier, which may constitute one or more accessory ingredients. In general, the formulations are prepared by uniformly bringing the active ingredients into association with liquid carriers or finely divided solid carriers or both, and then, if necessary, shaping the product.

Formulations suitable for oral administration may be used in discrete units such as capsules, cachets or tablets each containing a predetermined amount of active ingredient; as a powder or granule; as a solution or suspension in an aqueous or non-aqueous liquid; or as an oil-in-water or a water-in-oil liquid emulsion. The active ingredient may also be administered as a bolus or paste or may be contained within liposomes.

The formulations may be in unit dose or multi dose containers such as, for example, sealed ampules and vials, and may be stored in a lyophilized condition requiring only the addition of a sterile liquid carrier, such as water, suitable for injection immediately prior to use.

The compounds of this invention may be prepared by a variety of reaction schemes. One method particularly useful for preparing the compounds is illustrated is the following reaction sequence.

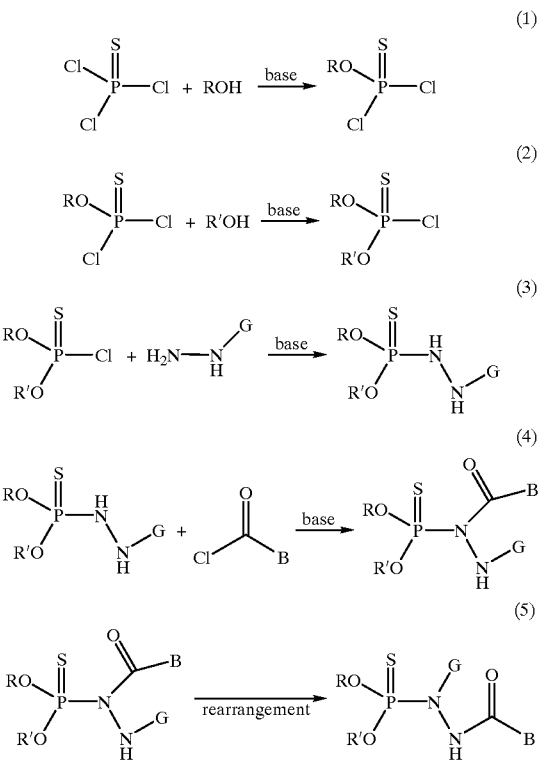

The above method is useful to react alcohols (or alkoxides) with thiophosphoryl chloride to prepare the corresponding thiophosphoryl analog (Steps 1 and 2). Analogous reactions using methylphosphonothioic dichloride, ethylphosphonothioic dichloride, phenylphosphonothioic dichloride, and related materials will yield the corresponding chlorides.

Bases to neutralize the hydrogen halide produced in the reaction may be chosen from organic or inorganic materials such as potassium carbonate, sodium hydroxide, sodium hydride, pyridine, triethylamine, diisopropylethylamine, 1,4-diazabicylco[2.2.2]octane, 1,8-diazabicyclo[5.4.0]undec-7-ene, 1,5-diazabicyclo[4.3.0]non-2-ene, and the like. Reaction temperatures for the above reactions may be varied from −70° C. to 120° C., preferably from −40° C. to 60° C. The appropriate base, solvent, and reaction parameters for a particular reaction may be selected on the basis of the chemical and physical properties of the reactants. Less preferred bases for reaction (4) are those which are less basic such as pyridine.

Step 4 in the above sequence is unique in that the acid chloride reacts with the nitrogen adjacent to the phosphorous rather than the expected nitrogen adjacent to the G group. Furthermore, the rearrangement of Step 5 also gives an unexpected product. In addition to the compounds of this invention, these two reactions may be used separately or combined to provide a broader selection of related compounds as follows (Reactions 6 and 7):

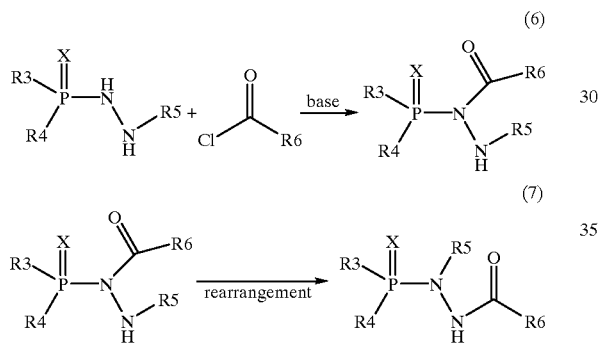

Therefore, another aspect of this invention is a method to prepare a compound of the formula:

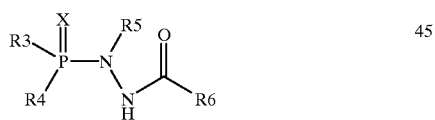

comprising the step of heating a compound of the formula:

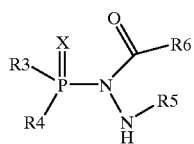

in the presence or absence of a solvent;
wherein:
X is O or S;
R3 and R4 are independently $(C_1-C_6)$ alkoxy, phenyloxy; $(C_1-C_6)$ alkyl, phenyl; N-$(C_1-C_6)$alkylamino; N,N-di$(C_1-C_6)$alkylamino; N-phenylamino; N-phenyl-N-$(C_1-C_6)$alkylamino; $(C_1-C_6)$ alkylthio; or phenylthio, each independently unsubstituted or substituted with one or more $(C_1-C_6)$ alkoxy, halo, $(C_1-C_6)$alkylthio, keto, carbo$(C_1-C_6)$alkoxy, or $(C_1-C_6)$ acyl groups; preferably R3 and R4 are independently $(C_1-C_6)$ alkoxy; $(C_1-C_6)$ alkyl, or phenyl, each independently unsubstituted or substituted with one or more $(C_1-C_6)$ alkoxy, keto, carbo$(C_1-C_6)$alkoxy, or $(C_1-C_6)$acyl groups;

R5 is $(C_1-C_8)$ primary alkyl; $(C_3-C_8)$ secondary alkyl; or $(C_4-C_8)$ tertiary alkyl, each unsubstituted or substituted with one or more of cyano, $(C_1-C_6)$alkoxy, $(C_1-C_6)$ alkylthio; halo; carbo$(C_1-C_6)$alkoxy, or $(C_1-C_6)$acyl groups; preferably R5 is $(C_3-C_6)$ secondary alkyl or $(C_4-C_8)$ tertiary alkyl, each unsubstituted or substituted with one or more cyano, $(C_1-C_6)$alkoxy, carbo$(C_1-C_6)$ alkoxy, or $(C_1-C_6)$acyl groups; and R6 is $(C_1-C_6)$alkyl; phenyl; or $(C_1-C_6)$alkoxy, each unsubstituted or substituted with one or more halo, $(C_1-C_6)$alkoxy, $(C_1-C_6)$alkyl, $(C_1-C_6)$alkylthio, nitro, cyano, or $(C_1-C_6)$alkylcarbonyl; preferably R6 is $(C_1-C_6)$ haloalkyl. The rearrangement step may be accomplished in the absence of a solvent. However, preferably a solvent will be used. When used, preferred solvents include diethyl ether, methylene chloride, tetrahydrofuran, and ethyl acetate. The temperature required to affect the reaction will depend upon the identity of the R3, R4 and R6 substituents; usually from −40° C. to 200° C. Preferably the temperature will be from −10° C. to 100° C.

A further aspect of this invention is a method to prepare a compound of the formula:

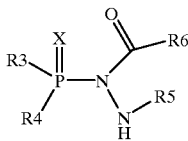

comprising contacting a compound of the formula:

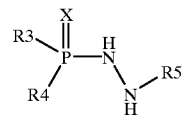

with an acyl chloride of the formula:

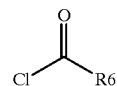

in the presence of a base;
wherein:
X is O or S;
R3 and R4 are independently $(C_1-C_6)$ alkoxy, phenyloxy; $(C_1-C_6)$ alkyl, phenyl; N-$(C_1-C_6)$alkylamino; N,N-di$(C_1-C_6)$alkylamino; N-phenylamino; N-phenyl-N-$(C_1-C_6)$alkylamino; $(C_1-C_6)$ alkylthio; or phenylthio, each independently unsubstituted or substituted with one or more $(C_1-C_6)$ alkoxy, halo, $(C_1-C_6)$alkylthio, keto, carbo$(C_1-C_6)$alkoxy, or $(C_1-C_6)$ acyl groups; preferably R3 and R4 are independently $(C_1-C_6)$ alkoxy; $(C_1-C_6)$ alkyl, or phenyl, each independently unsubstituted or substituted with one or more of $(C_1-C_6)$ alkoxy, keto, carbo$(C_1-C_6)$alkoxy, and $(C_1-C_6)$acyl groups;

R5 is $(C_1-C_8)$ primary alkyl; $(C_3-C_8)$ secondary alkyl; or $(C_4-C_8)$ tertiary alkyl, each unsubstituted or substituted with one or more of cyano, $(C_1-C_6)$alkoxy, $(C_1-C_6)$ alkylthio; halo; carbo$(C_1-C_6)$alkoxy, or $(C_1-C_6)$acyl groups; preferably R5 is $(C_3-C_6)$ secondary alkyl or $(C_4-C_6)$ tertiary alkyl, each unsubstituted or substituted with one or more of cyano, $(C_1-C_6)$alkoxy, carbo $(C_1-C_6)$alkoxy, and $(C_1-C_6)$acyl groups; and R6 is $(C_1-C_6)$alkyl; phenyl; or $(C_1-C_6)$alkoxy, each unsubstituted or substituted with one or more halo, $(C_1-C_6)$alkoxy, $(C_1-C_6)$alkyl, $(C_1-C_6)$alkylthio, nitro, cyano, or $(C_1-C_6)$alkylcarbonyl; preferably R6 is $(C_1-C_6)$ haloalkyl.

The base is selected from amidines and guanidines, amines, alkoxides, hydroxides, and metal hydrides. Preferred bases include triethyl amine, diisopropylethyl amine, and sodium hydride. The reaction may be accomplished in the absence of a solvent. However, preferably a solvent which does not react with the base will be used. Preferred solvents include diethyl ether, methylene chloride, tetrahydrofuran, and ethyl acetate.

The required starting materials and intermediates to prepare the compounds of the invention are available from commercial sources or may be prepared by known reactions. Other suitable reaction schemes will be obvious to the chemist of ordinary skill.

The following examples are intended only to further illustrate the invention.

EXAMPLE A

Preparation of O-ethyl O-propyl Chlorothiophosphate

To 30 g (167 mmole) of O-ethyl dichlorothiophosphate in 100 ml of tetrahydrofuran (THF) cooled to −70° C. was added a solution of sodium propoxide (from 7.4 g of 60% NaH (184 mmole) and 11 g (176 mmole) of 1-propanol) in 50 ml of THF. After warming to room temperature over 2 hours, the THF was removed in vacuo and the residue was partitioned between 50 ml diethyl ether, 50 ml hexanes, and 25 ml cold water. The organic layer was dried over magnesium sulfate, concentrated in vacuo, and distilled (bp 45–50° C. 1 torr) yielding 20 g of the title compound, an oil. nmr 1.0 t 3H, 1.4 t 3H, 1.8 sextet 2H, 4.4 m 4H.

EXAMPLE B

Preparation of O,O-diisopropyl Chlorothiophosphate

A solution of sodium isopropoxide in THF was prepared by the reaction of 45 g (1125 mmole) of 60% sodium hydride with 84 ml (1100 mmole) of isopropyl alcohol in 400 ml of THF. This solution was added, with mechanical stirring, to 83.4 g (490 mmole) of thiophosphorylchloride in 300 ml of THF and the mixture was cooled to −40° C. After the addition was complete the reaction mixture was slowly warmed to 25° C. When gas chromatography showed the reaction to be complete the THF was removed in vacuo and the product partitioned between hexanes and water. The organic layer was dried over anhydrous magnesium sulfate and concentrated in vacuo yielding 93 g of the title compound, an oil. nmr 1.4 d 12H, 4.9 m 2H.

EXAMPLE C

Preparation of O-ethyl O-neopentyl Chlorothiophosphate

By substantially following the procedure of Example A, using neopentyl alcohol in place of 1-propanol, one obtains the title compound, an oil. nmr 1.0 s 9H, 1.4 m 3H, 3.9 m 2H, 4.4 m 2H.

EXAMPLE D

Preparation of O-ethyl O-isopropyl Chlorothiophosphate

By substantially following the procedure of Example A, using isopropyl alcohol in place of 1-propanol, one obtains the title compound, an oil. nmr 1.4 m 9H, 4.3 m 2H, 5.0 m 1H.

EXAMPLE E

Preparation of O-ethyl O-isobutyl Chlorothiophosphate

By substantially following the procedure of Example A, using isobutyl alcohol in place of 1-propanol, one obtains the title compound, an oil. nmr 1.0 m 6H, 1.4 m 3H, 2.1 m 1H, 4.0 m 2H, 4.3 m 2H.

EXAMPLE F

Preparation of 2-(O,O-diethylthiophosphoryl)-1-tert-butyl Hydrazine

Into a two liter three necked mechanically stirred flask were added 153.2 g (1230 mmole) of tertbutylhydrazine hydrochloride, 500 ml of methylene chloride, and a mixture of 199 g of 50% aqueous sodium hydroxide and 200 g of water. After stirring for five minutes, 201.3 g (1079 mmole) of O,O-diethylthiophosphoryl chloride was added at a rate of about two drops per second. The addition required 50 minutes. After stirring an additional 30 minutes, 200 ml of water was added and the layers separated. The organic layer was washed twice with 200 ml of water, dried over anhydrous magnesium sulfate, and concentrated to yield 254.3 g of the title compound, a yellow solid. mp 33–34° C. nmr 1.10 s 9H, 1.34 t 6H, 3.0 bs 1H, 4.1 m 4H, 4.6 d 1H.

Compound 1: Preparation of 1-(O,O-diethylthiophosphoryl)-1-tertbutyl-2-trichloroacetyl Hydrazine Into a two liter three necked mechanically stirred flask were added 254 g (1060 mmole) of 2-(O,O-diethylthiophosphoryl)-1-tertbutyl hydrazine, 800 ml of diethyl ether, and 131 g (1297 mmole) of triethylamine. After stirring for five minutes, 204 g (1121 mmole) of trichloroacetyl chloride was added at a rate of about two drops per second. The addition required 55 minutes and was accompanied by gentle refluxing. After stirring for an additional 75 minutes, 500 ml of water was added. The layers were separated and the organic layer was washed twice with 100 ml of dilute hydrochloric acid and once with 100 ml of saturated aqueous sodium chloride. After drying with anhydrous magnesium sulfate, concentration in vacuo, and crystallization from hexanes one obtains 208 g of the title compound, a white solid. mp 120–121.5° C. nmr 1.35 t 6H, 1.39 s 9H, 4.2 m 4H, 8.1 s 1H. Downfield singlets in the neighborhood of 7–8δ indicate the desired rearranged isomer. Doublets in the 4–5δ range indicate an undesired isomer.

Compounds 10/11: Preparation of 1-(O,O-diethylthiophosphoryl)-1-tertbutyl-2-dichloroacetyl Hydrazine and 1-(O,O-diethylthiophosphoryl)- 1-tertbutyl-2-monochloroacetyl Hydrazine Into a 100 ml round bottomed flask with magnetic stirring were added 12.06 g (31 mmole) of 1-(O,O- diethylthiophosphoryl)-1-tertbutyl-2-trichloroacetyl hydrazine (Compound 1), 20 ml of anhydrous ethanol, and 4.5 ml glacial acetic acid (79 mmole). The mixture was cooled to 0° C. To this stirred mixture was added 2.25 g (34.5 mmole) of zinc powder. After stirring for one hour, the zinc was consumed. Concentration in vacuo, dilution with diethyl ether, extraction with aqueous sodium bicarbonate, washing with brine, drying with anhydrous magnesium sulfate, and concentration in vacuo yielded a mixture of starting material and the reduced dichloro, monochloro, and fully reduced acetyl compounds. Separation by column chromatography on silica gel using a mixture of ethyl acetate and hexanes for elution gave the title compounds: 1-(O,O-diethylthiophosphoryl)-1-tertbutyl-2-dichloroacetyl hydrazine, a white solid mp 118–119.5° C. nmr 1.35 t 6H, 1.39 s 9H, 4.2 m 4H, 6.05 s 1H, 7.9 s 1 H and 1-(O,O-diethylthiophosphoryl)-1-tertbutyl-2-monochloroacetyl hydrazine, a white solid mp 68–70 ° C. nmr 1.35 t 6H, 1.39 s 9H, 4.1 s 2H, 4.2 m 4H, 7.8 s 1H.

Compound 23: Preparation of 1-(O-ethoxy-O-ethylthiophosphonyl)-1-tertbutyl-2-dichloroacetyl Hydrazine Into a 100 ml round bottomed flask with magnetic stirring were added 1.54 g (4.5 mmole) of 1-(O-ethoxy-O-ethylthiophosphonyl)-1-tertbutyl-2-trichloroacetyl hydrazine (Compound 21), 5 g of toluene 0.54 g (5.4 mmole) of triethylamine, and 0.84 g (6.1 mmole) of diethyl phosphite. The mixture was refluxed for 70 minutes, washed with water, concentrated in vacuo and chromatographed yielding 0.98 g of the title compound a white solid, mp 124–126° C.

Biological Evaluations

Test Solutions

A parent solution containing 600 parts per million (ppm) of the test compound was made by dissolving the test compound in a solvent (acetone: methanol,1:1) and adding water to give an acetone:methanol:water system of 5:5:90 and then a surfactant was utilized at the equivalent of 7.8 ml per 100 liters of test solution. The surfactant consisted of a 1:1 mixture of an alkylarylpolyetheralcohol (Rohm and Haas Co. Triton® X-155) and a modified phthalic glycerol alkyl resin (Rohm and Haas Co. Triton® B-1956).

Test solutions were made by serially diluting the 600 ppm parent solution with water, solvent, and surfactant to give concentrations of 150 and 38 ppm.

Nematode Screening Test

For the nematode test, soil was homogeneously inoculated with nematode eggs (Southern Root-Knot Nematode *Meloidogyne incognita*) at a rate of 20000 eggs per 200 milliliters (ml) of soil extracted from a macerated blend of tomato roots heavily knotted with the root-knot nematode. Ten ml of the 150 ppm test solution were added to 200 ml of the inoculated soil in a 16 oz. jar to give a concentration by volume of 11400 grams per hectare (gm/ha). If needed, ten ml of the 38 ppm test solution were added to soil in another jar providing a concentration by volume of 2850 gm/ha. The jars were shaken to ensure thorough mixing, immediately uncapped, and allowed to air for two hours. The soil was placed into a 7.5 cm plastic pot and three cucumber (*Cucumis sativus*) seeds were planted. The pots were held under greenhouse conditions for 21 days. Upon termination, the cucumber roots were examined for the presence of knots. Results are summarized in Table 2 and are expressed as percent knot reduction.

Mexican Bean Beetle Test

The test solution was sprayed using a moving single boom tee jet sprayer at a volume equivalent to 935 liters/ha onto a petri dish containing a lima bean (*Phaseolus limensis* var: Woods' Prolific) leaf placed on a moistened piece of filter paper. After the leaf dried it was infested with ten beetles (*Epilachna varivestis*) and covered. The percent control was evaluated 48 hours after infestation.

Potato Leafhopper Test

The test solution was sprayed using a moving single boom tee jet sprayer at a volume equivalent to 935 liters/ha onto a petri dish containing a fava bean (*Vicia faba*) leaf placed on a moistened piece of filter paper. After the leaf dried it was infested with five mixed nymphs (*Empoasca fabae*) and covered. The percent control was evaluated 72 hours after infestation.

Corn Rootworm Screening Test

Ten ml of each test solution were pipetted into 190 gm of a non-sterile loamy soil (pH 5.5 to 7.0) contained in a 500 ml glass jar. The 150 ppm test solution provided a soil concentration of 11400 gm/Ha. The 38 ppm test solution provided a soil concentration of 2850 gm/ha. Each jar was shaken to insure uniform distribution of chemical in the soil. Soil moisture ranged from 18% to 22%.

In this soil, organophosphate and carbamate soil insecticides (e.g., Dyfonate® and Furadan®), used as test standards, effectively controlled the corn rootworm. This soil was considered a "non-aggressive soil".

The southern corn rootworm, *Diabrotica undecimpunctata howardi*, was used as the test insect. Two presoaked corn (*Zea mays* var. Golden Cross Bantam) seeds were placed in the bottom of a 30 ml. plastic cup and covered with about 30 gm. of treated soil. The soil surface of each cup was inoculated with southern corn rootworm eggs resulting in a larval challenge of 50 to 70 larvae per cup. The cups were closed with tight fitting snap caps.

The test cups were held for 10 days at 27° C. and then the percent kill relative to the infested check was determined. Mortalities obtained were plotted on logarithmic probability paper (No. 3228, Codex Book Co. Inc., Norwood, Mass.). The estimated concentration eliciting a 90% mortality (LC90) was established from the best eye-fitted line to the plotted mortality data.

TABLE 2

| Compound # | Percent Control of Mexican bean beetle at 600 grams per hectare | Percent Control of Potato leaf hopper at 600 grams per hectare | Percent Control of Corn Rootworm at 11400 grams per hectare | Percent Control of Root Knot Nematode at 11400 grams per hectare |
|---|---|---|---|---|
| 1 | 100 | NT | 100 | 98 |
| 2 | 100 | NT | 87 | 0 |
| 3 | 100 | NT | 98 | 74 |
| 4 | 100 | NT | 0 | 0 |
| 5 | 100 | NT | 96 | 0 |
| 6 | 100 | NT | 100 | 54 |
| 7 | 80 | NT | 96 | 0 |
| 8 | 30 | NT | 0 | 98 |
| 9 | 100 | NT | 100 | 100 |
| 10 | 100 | NT | 0 | 100 |
| 11 | NT | 100 | 0 | 43 |
| 12 | NT | 100 | 100 | 0 |
| 13 | NT | 100 | 0 | 100 |
| 14 | NT | 100 | 0 | 0 |
| 15 | NT | 100 | 0 | 0 |
| 16 | NT | 100 | 66 | 0 |
| 17 | NT | 60 | 0 | 0 |
| 18 | NT | 100 | 0 | 25 |
| 19 | NT | 100 | 0 | 90 |
| 20 | NT | 100 | 0 | NT |
| 21 | NT | 100 | 0 | NT |
| 22 | NT | 100 | 0 | NT |

TABLE 2-continued

| Compound # | Percent Control of Mexican bean beetle at 600 grams per hectare | Percent Control of Potato leaf hopper at 600 grams per hectare | Percent Control of Corn Rootworm at 11400 grams per hectare | Percent Control of Root Knot Nematode at 11400 grams per hectare |
|---|---|---|---|---|
| 23 | NT | 40 | 0 | NT |

NT = not tested

Anthelmintic Test

Compounds were tested as inhibitors of larval development in *Haemonchus contortus* (McMaster, benzimidazole susceptible) isolates, *Trichostrongylus colubriformis* (McMaster susceptible) and *Ostertagia circumcincta* (Glenlothian susceptible).

Eggs of the parasitic helminths, isolated from sheep feces, were applied to wells of a microtiter plate which contained a gradient of concentrations of the test compound in nutrient solution. After the eggs hatched, L1 larvae developed through to the L3 stage over 6 days. Development was inhibited and a minimum inhibitory concentration in ppm was determined. The results are in Table 3. See for example, E. Lacey et al p 177–184 in: *Resistance of Parasites to Antiparasitic Drugs*, edited by J. C. Boray MSD AGVET, Rahway, N.J.

TABLE 3

| | *H. contortus* | *T. colubriformis* | *O. circumcinta* |
|---|---|---|---|
| Compound | MIC | MIC | MIC |
| 10 | 1.56 | 12.5 | 1.56 |

We claim:

1. A compound of the formula:

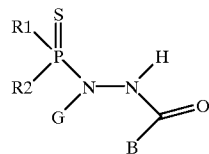

(I)

wherein:
R1 is unsubstituted or substituted ($C_1$–$C_6$) alkoxy wherein the substituents are independently one or more ($C_1$–$C_6$) alkoxy, keto, carbo($C_1$–$C_6$)alkoxy, or ($C_1$–$C_6$)acyl groups;

R2 is ($C_1$–$C_6$) alkoxy, ($C_1$–$C_6$) alkyl, or phenyl, each of which is unsubstituted or substituted with one or more ($C_1$–$C_6$) alkoxy, keto, carbo($C_1$–$C_6$)alkoxy, or ($C_1$–$C_6$) acyl groups;

G is ($C_3$–$C_6$) secondary alkyl or ($C_4$–$C_6$) tertiary alkyl, each of which is unsubstituted or substituted with one or more cyano, ($C_1$–$C_6$) alkoxy, carbo($C_1$–$C_6$)alkoxy, or ($C_1$–$C_6$)acyl groups;

B is ($C_1$–$C_6$) haloalkyl;

its enantiomers and stereoisomers;

and agronomically acceptable salts thereof.

2. The compound of claim 1 wherein R1 and R2 are independently ($C_1$–$C_2$)alkoxy; G is ($C_4$–$C_6$)tertiary alkyl, and B is halo($C_1$)alkyl.

3. The compound of claim 1 wherein R1 and R2 are identical and selected from methoxy and ethoxy, G is tertiary butyl, and B is dichloromethyl or trichloromethyl.

4. A composition comprising an insecticidally, acaricidally, or nematocidally effective amount of one or more compounds of claim 1 and an agronomically acceptable carrier or an anthelmintically effectively amount of one or more compounds of claim 1 and a pharmaceutically acceptable carrier.

5. A method for controlling a pest comprising applying to the pest or to the soil or to the foliage of plants to be freed from infestation by the pest, a pesticidally effective amount of one or more compounds of claim 1 and wherein the pest is selected from insects, acarids, and nematodes.

6. A method for controlling a helminth, comprising contacting the helminth with an effective amount of a compound of claim 1.

7. A method to prepare a compound of the formula:

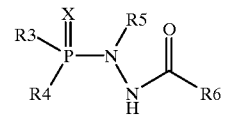

comprising the step of heating a compound of the formula:

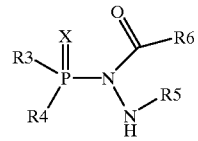

in the presence or absence of a solvent;

wherein:

X is O or S;

R3 and R4 are independently ($C_1$–$C_6$) alkoxy, phenyloxy; ($C_1$–$C_6$) alkyl, phenyl; N-($C_1$–$C_6$)alkylamino; N,N-di ($C_1$–$C_6$)alkylamino; N-phenylamino; N-phenyl-N-($C_1$–$C_6$)alkylamino; ($C_1$–$C_6$)alkylthio; or phenylthio, each independently unsubstituted or substituted with one or more of ($C_1$–$C_6$) alkoxy, halo, ($C_1$–$C_6$)alkylthio, keto, carbo($C_1$–$C_6$)alkoxy, or ($C_1$–$C_6$)acyl groups;

R5 is ($C_1$–$C_8$) primary alkyl; ($C_3$–$C_8$) secondary alkyl; or ($C_4$–$C_8$) tertiary alkyl, each unsubstituted or substituted with one or more cyano, ($C_1$–$C_6$)alkoxy, ($C_1$–$C_6$) alkylthio; halo; carbo($C_1$–$C_6$)alkoxy, or ($C_1$–$C_6$)acyl groups; and R6 is ($C_1$–$C_6$)alkyl; phenyl; or ($C_1$–$C_6$)alkoxy, each unsubstituted or substituted with one or more halo, ($C_1$–$C_6$)alkoxy, ($C_1$–$C_6$)alkyl, ($C_1$–$C_6$)alkylthio, nitro, cyano, or ($C_1$–$C_6$)alkylcarbonyl.

8. A method to prepare a compound of the formula:

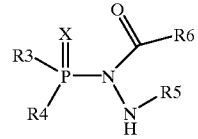

comprising contacting a compound of the formula:

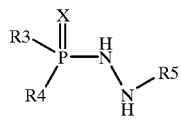

with an acyl chloride of the formula:

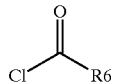

in the presence of a base;
wherein:

X is O or S;

R3 and R4 are independently $(C_1-C_6)$ alkoxy, phenyloxy; $(C_1-C_6)$ alkyl, phenyl; N-$(C_1-C_6)$alkylamino; N,N-di$(C_1-C_6)$alkylamino; N-phenylamino; N-phenyl-N-$(C_1-C_6)$alkylamino; $(C_1-C_6)$alkylthio; or phenylthio, each independently unsubstituted or substituted with one or more $(C_1-C_6)$ alkoxy, halo, $(C_1-C_6)$alkylthio, keto, carbo$(C_1-C_6)$alkoxy, or $(C_1-C_6)$acyl groups;

R5 is $(C_1-C_8)$ primary alkyl; $(C_3-C_8)$ secondary alkyl; or $(C_4-C_8)$ tertiary alkyl, each unsubstituted or substituted with one or more cyano, $(C_1-C_6)$alkoxy, $(C_1-C_6)$ alkylthio; halo; carbo$(C_1-C_6)$alkoxy, or $(C_1-C_6)$acyl groups; and R6 is $(C_1-C_6)$alkyl; phenyl; or $(C_1-C_6)$alkoxy, each unsubstituted or substituted with one or more halo, $(C_1-C_6)$alkoxy, $(C_1-C_6)$alkyl, $(C_1-C_6)$alkylthio, nitro, cyano, or $(C_1-C_6)$alkylcarbonyl.

9. A method to prepare a compound of the formula:

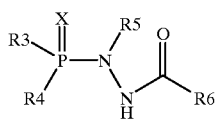

comprising the steps of:

a) contacting a compound of the formula:

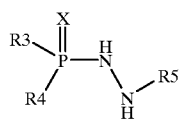

with an acyl chloride of the formula:

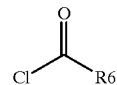

in the presence of a base;
to form a compound of the formula:

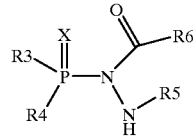

and
b) heating the compound of the formula:

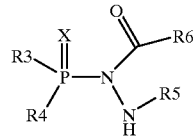

in the presence or absence of a solvent;
wherein:

X is O or S;

R3 and R4 are independently $(C_1-C_6)$ alkoxy, phenyloxy; $(C_1-C_6)$ alkyl, phenyl; N-$(C_1-C_6)$alkylamino; N,N-di$(C_1-C_6)$alkylamino; N-phenylamino; N-phenyl-N-$(C_1-C_6)$alkylamino; $(C_1-C_6)$alkylthio; or phenylthio, each independently unsubstituted or substituted with one or more of $(C_1-C_6)$ alkoxy, halo, $(C_1-C_6)$alkylthio, keto, carbo$(C_1-C_6)$alkoxy, or $(C_1-C_6)$acyl groups;

R5 is $(C_1-C_8)$ primary alkyl; $(C_3-C_8)$ secondary alkyl; or $(C_4-C_8)$ tertiary alkyl, each unsubstituted or substituted with one or more cyano, $(C_1-C_6)$alkoxy, $(C_1-C_6)$ alkylthio; halo; carbo$(C_1-C_6)$alkoxy, or $(C_1-C_6)$acyl groups; and R6 is $(C_1-C_6)$alkyl; phenyl; or $(C_1-C_6)$alkoxy, each unsubstituted or substituted with one or more halo, $(C_1-C_6)$alkoxy, $(C_1-C_6)$alkyl, $(C_1-C_6)$alkylthio, nitro, cyano, or $(C_1-C_6)$alkylcarbonyl.

10. The method of claim 7, 8, or 9 wherein:

X is S;

R3 and R4 are independently $(C_1-C_6)$ alkoxy; $(C_1-C_6)$ alkyl, or phenyl, each independently unsubstituted or substituted with one or more $(C_1-C_6)$ alkoxy, keto, carbo$(C_1-C_6)$alkoxy, or $(C_1-C_6)$acyl groups;

R5 is $(C_3-C_6)$ secondary alkyl or $(C_4-C_6)$ tertiary alkyl, each unsubstituted or substituted with one or more cyano, $(C_1-C_6)$alkoxy, carbo$(C_1-C_6)$alkoxy, or $(C_1-C_6)$acyl groups; and R6 is $(C_1-C_6)$ haloalkyl.

* * * * *